(12) United States Patent
Ho

(10) Patent No.: US 8,591,133 B2
(45) Date of Patent: Nov. 26, 2013

(54) AUTOMATIC SWITCH FOR A POWER CIRCUIT USABLE IN A BOTTLE

(76) Inventor: Jui-Sheng Ho, Taichung (TW)

( * ) Notice: Subject to any disclaimer, the term of this patent is extended or adjusted under 35 U.S.C. 154(b) by 471 days.

(21) Appl. No.: 13/024,327

(22) Filed: Feb. 10, 2011

(65) Prior Publication Data

US 2012/0207532 A1 Aug. 16, 2012

(51) Int. Cl.
*B43K 7/10* (2006.01)
(52) U.S. Cl.
USPC .......................................... 401/214; 401/209
(58) Field of Classification Search
USPC .......... 401/208, 209, 213, 214, 215, 216, 219
See application file for complete search history.

(56) References Cited

U.S. PATENT DOCUMENTS

| 4,722,326 | A * | 2/1988 | Ruderian ........................ 601/16 |
| 2007/0098483 | A1 * | 5/2007 | Milesi et al. .................. 401/209 |

* cited by examiner

*Primary Examiner* — David Walczak

(57) ABSTRACT

An automatic switch for a power circuit of a bottle container is provided. The bottle container includes a bottle body, a cover and an electronic unit for allowing an accommodating unit to be assembled between the bottle body and the cover. A liquid is received in the bottle body. A ball is disposed in a mouth at a front end of the cover, and the ball is capable of opening/closing the mouth by means of an elastic body. The elastic body has a first conductive portion and a second conductive portion. The first conductive portion is brought into electrical contact with a positive electrode (or negative electrode) of a power source of the electronic unit. The second conductive portion is located above the negative electrode (or positive electrode) of the power source of the electronic unit by a distance when the elastic body is not pressed.

6 Claims, 7 Drawing Sheets

AUTOMATIC SWITCH FOR A POWER CIRCUIT USABLE IN A BOTTLE

BACKGROUND OF THE INVENTION

1. Field of the Invention

The present invention relates to a bottled container, and in particular to an electrical switch for a power circuit in a bottled container, which is capable of also generating vibrations or light.

2. Description of the Prior Art

When a user applies skin-care lotion onto his or her face or other regions, the user typically pours the skin-care lotion onto the palm and then applies the skin-care lotion over the desired region, such as the face. Then, the user rubs and pats the face with the fingers or massages the face with a massaging implement, thereby increasing the rate of absorption of the skin-care lotion by the skin. Although a massaging device may significantly improve the effects of the skin-care lotion, it inevitably increases costs. On the other hand, when the skin-care lotion is not in use, some of the constituents may be settle out in the bottled container due to their differing densities. As a result, the beneficial effects of the skin-care lotion may deteriorate if the skin-care lotion is not well mixed the next time.

Taiwan Patent No. M371460 discloses a vibrating container. As shown in FIG. 1, the interior of a body 11 of the container 1 is filled with a skin-care lotion. An outlet end of the body 11 is provided with an applicator head 2. The distal end of the body 11 is provided with a locking base 111. The locking base 111 allows a vibrating source 31 of a vibrating device 3 to be received therein. The vibrating source 31 is provided with a switch 311, and one end of the vibrating source 31 is connected to a vibrator 33 through an electric wire 32. The vibrator 33 is fixedly connected to the body 11. When the user intends to use the vibrating container 1, he/she presses the switch 311, so that the vibrator 33 generates vibrations by means of the vibrating source 31 and the electric wire 32. The vibrator 33 is fixedly connected or adhered to the body 11, so that the vibrations of the vibrator 33 are directly transmitted to the bottle body 11, thereby mixing the skin-care lotion disposed in the body 11. Then, the user is ready to hold the body 11 while using the applicator 2 to spread the well-mixed skin-care lotion on the skin. However, such a bottled container has a problem in that the user has to turn on or off the switch with every use of the bottled container. Therefore, the conventional bottled container is inconvenient to use, and needs to be improved.

SUMMARY OF THE INVENTION

In order to solve the above problems, a primary objective of the present invention is to provide an automatic switch for a power circuit used in a bottle container, whereby the electrical conduction of the power circuit can be automatically generated when in use and automatically shut off when not in use. Thus, the present invention provides improved convenience.

In order to achieve the above objective, the present invention provides an automatic switch for a power circuit in a bottle container. The container includes a bottle body, a cover and an electronic unit received between the bottle body and the cover through an accommodating unit. A ball and an elastic body are disposed between the cover and the accommodating unit. A liquid is received in the bottle body. The ball is received in a mouth at a front end of the cover. The ball is capable of elastically opening/closing the mouth by means of the elastic body. The accommodating unit includes an accommodating body and an accommodating base. The accommodating body is provided with a first accommodating portion, a second accommodating portion, a third accommodating portion, and a fourth accommodating portion for allowing a first conducting portion of one end of the elastic body and components of the electronic unit to be received therein. The accommodating portions and the accommodating body are disposed in the accommodating base for assembly. The electronic unit includes a motor (or a lamp), a battery serving as a power source, a first conductor, a second conductor and a third conductor. The first conductor is disposed in the first accommodating portion with one of its end penetrating to face the second conductor. The motor is disposed in the third accommodating portion. The outer periphery of the motor is electrically conductive. One end of the motor corresponding to the first conductor is planar for electrically contacting one end surface of the first conductor. The other end of the motor is provided with a vibrating shaft. The third conductor allows the battery to be accommodated therein in such a manner that the positive electrode (or negative electrode) of the battery is brought into contact with the third conductor. The second conductor is formed into an L shape. One end of the second conductor is brought into electrical contact with the surface of the negative electrode (or positive electrode) of the battery. The other end of the third conductor is provided with an electrical connection portion for contacting the outer surface of the motor, so that the electric current can flow from the negative electrode of the battery through the motor to the first conductor. The elastic body has a first conductive portion and a second conductive portion. The first conductive portion may be integrally formed at the distal end of the elastic body or be separate from the elastic body. The first conductive portion is disposed through the first accommodating portion of the accommodating body for contacting the third conductor of the positive electrode (or negative electrode) of the power source. When the elastic body is not pressed, the second conductive portion is located above the first conductor of the negative electrode (or positive electrode) of the power source of the electronic unit by a distance. With this structure, when the user applies the liquid in the bottled container, the ball is brought into contact with the skin of the user while the elastic body is compressed to electrically contact the second conductive portion with the first conductor, thereby generating automatically electrically conducting and activating the power circuit. In this way, the motor or the lamp can be turned on automatically when the bottled container is used. Thus, the present invention has improved convenience and practicability.

DETAILED DESCRIPTION OF THE INVENTION

Figure 1:
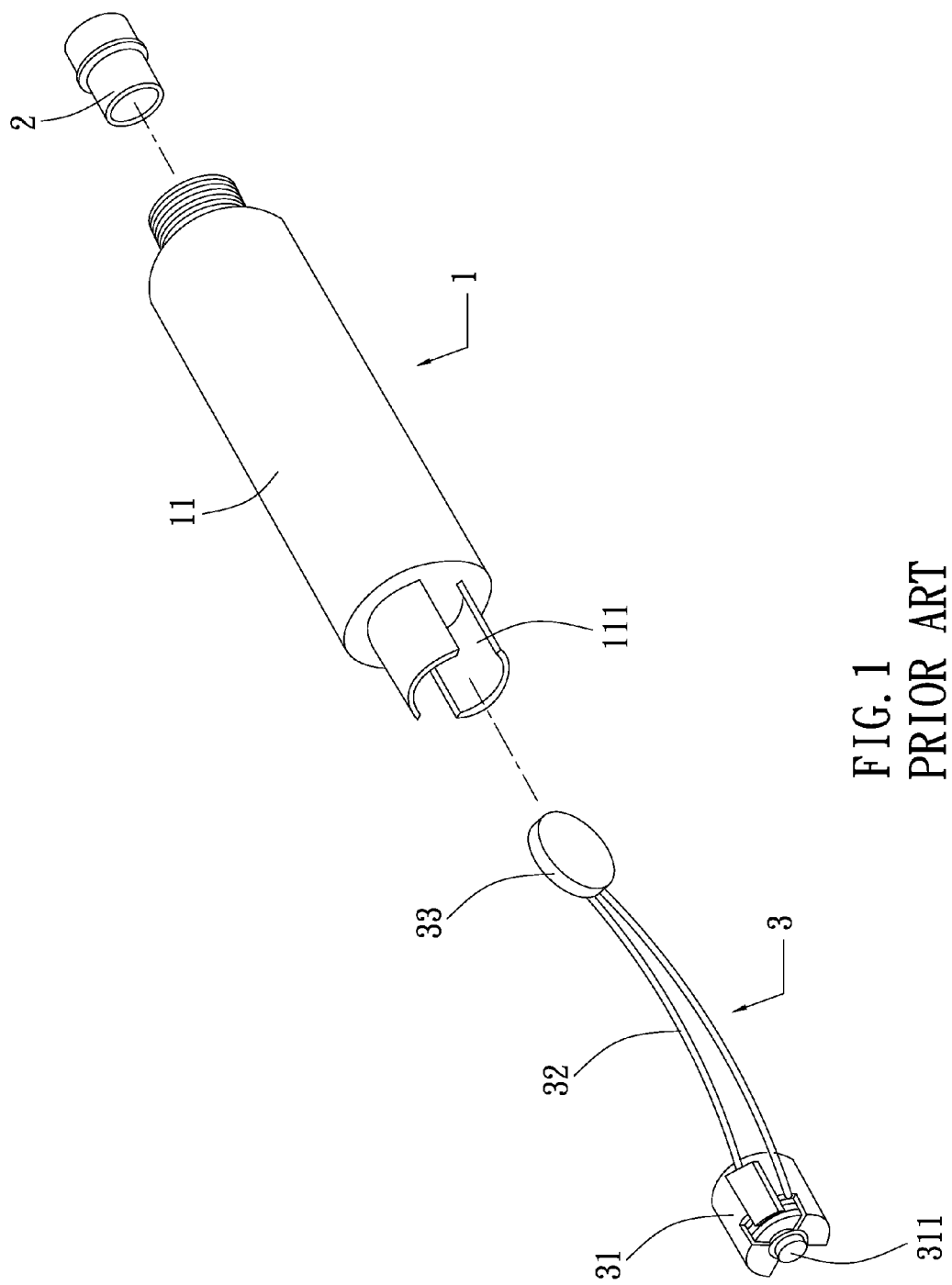
FIG. 1 is an exploded perspective view of a prior art device.
Figure 2:
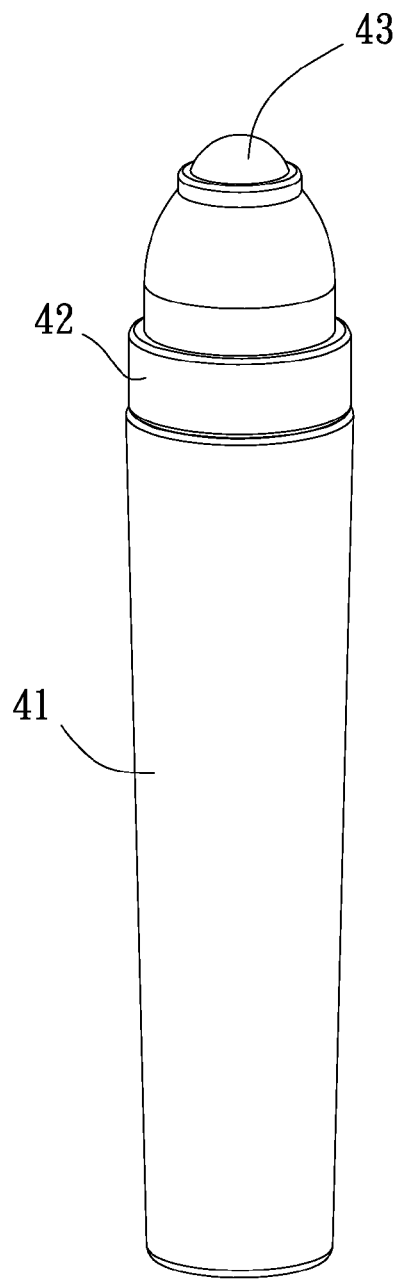
FIG. 2 is a perspective view showing the external appearance of an embodiment of the present invention

Please refer to FIGS. 2 to 7. Embodiments of the present invention provide an automatic switch for a power circuit used in a bottle container. The bottle container includes a bottle body 41, a cover 42, a ball 43, an elastic body 50, an accommodating unit 60 and an electronic unit 70.

The interior of the bottle body 41 is hollow for accepting a skin-care lotion to be received therein. The accommodating unit 60 is received in an open end of the bottle body 41 onto which the cover 42 is threadedly connected.

The cover 42 is a common cover for a bottled container. The interior of the cover 42 is hollow to form an axial space. A mouth 421 of the cover 42 allows the ball 43 to be received therein.

The ball 43 is a rolling ball. With the elastic force of the elastic body 50, the ball 43 is capable of opening and closing the mouth 421.

Figure 3:
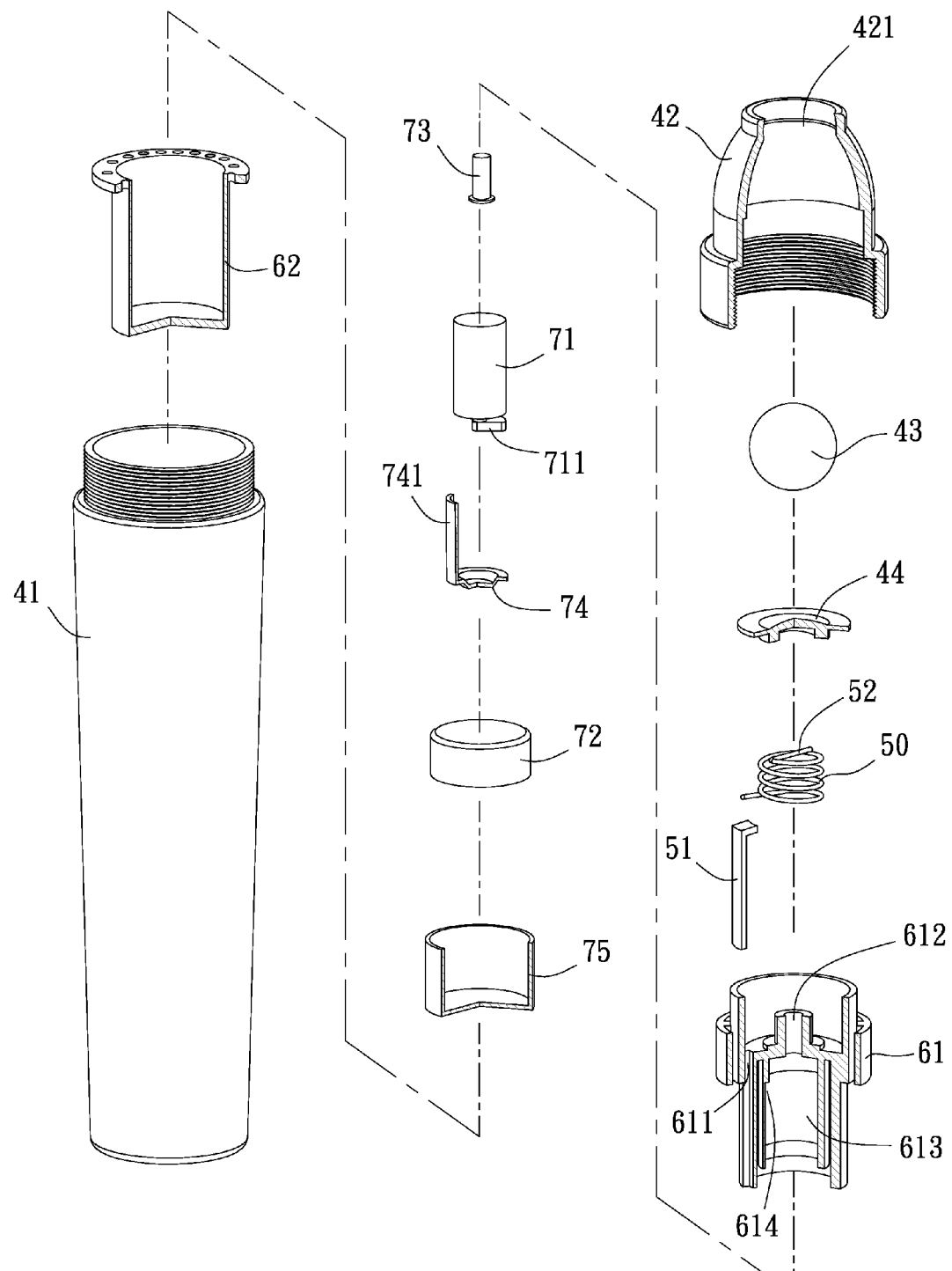
FIG. 3 is an exploded perspective view of an embodiment of present invention.
Figure 4:
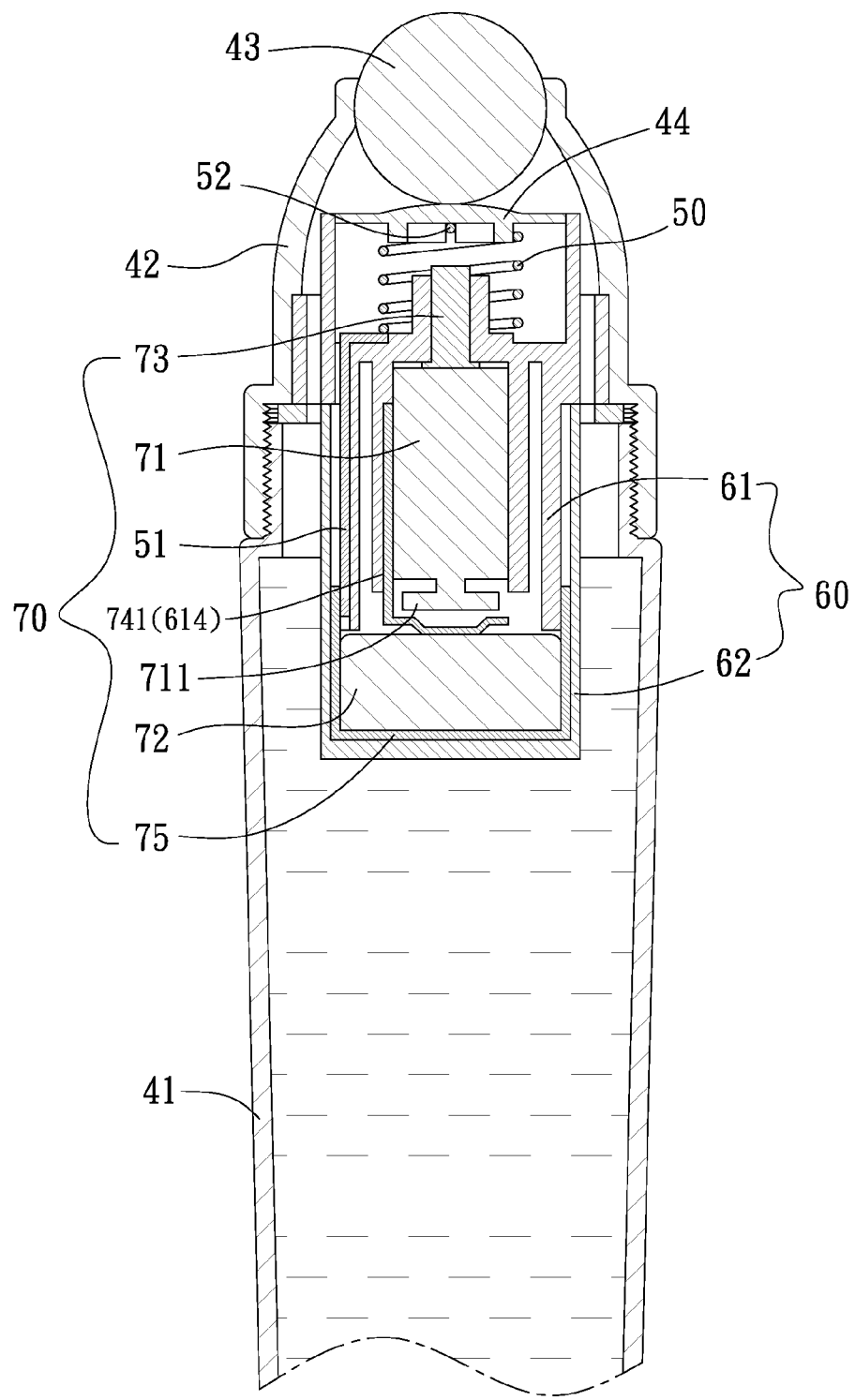
FIG. 4 is an assembled cross-sectional view of an embodiment of present invention in which a power source is not electrically connected.
Figure 5:
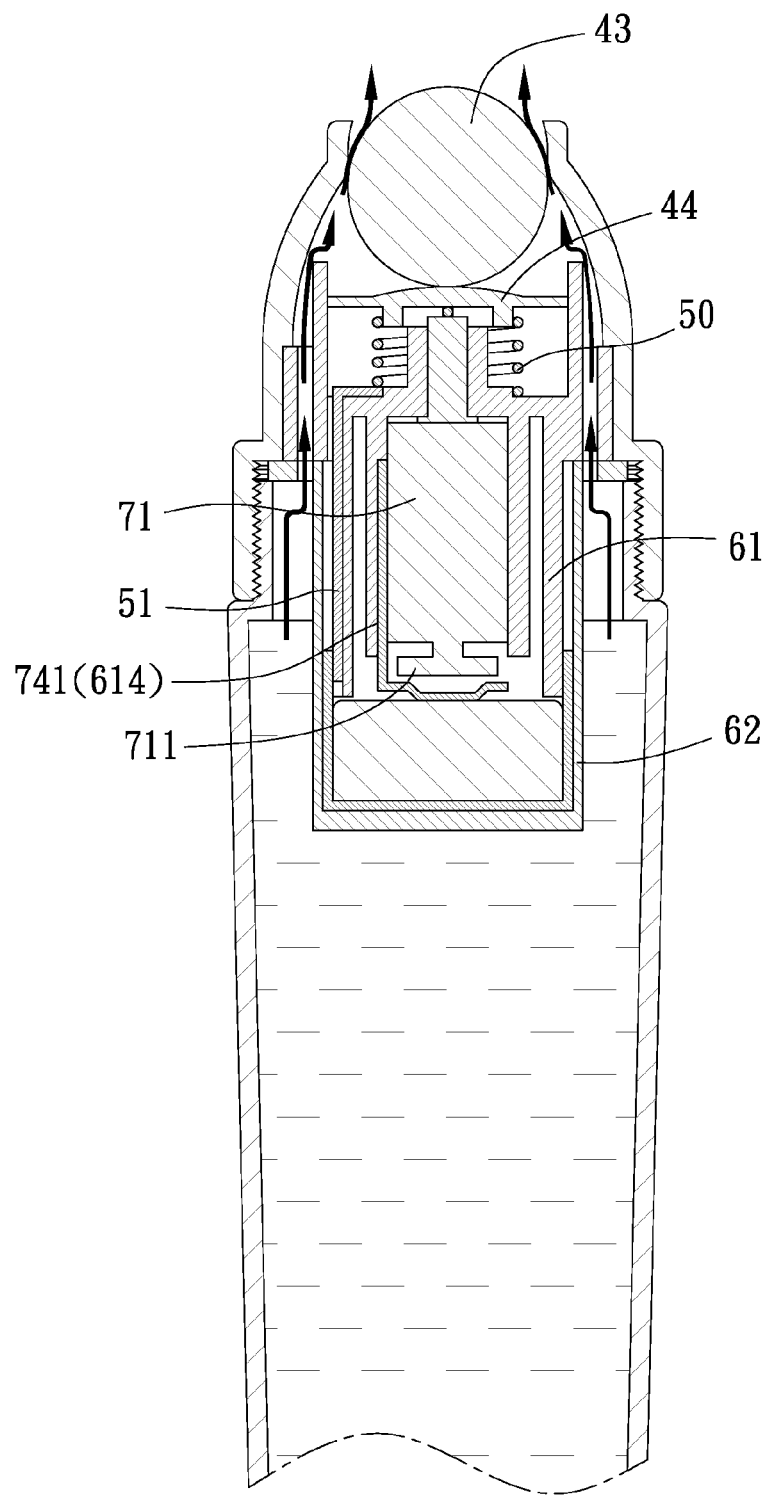
FIG. 5 is another assembled cross-sectional view of an embodiment of present invention in which the power source is electrically connected.
Figure 7:
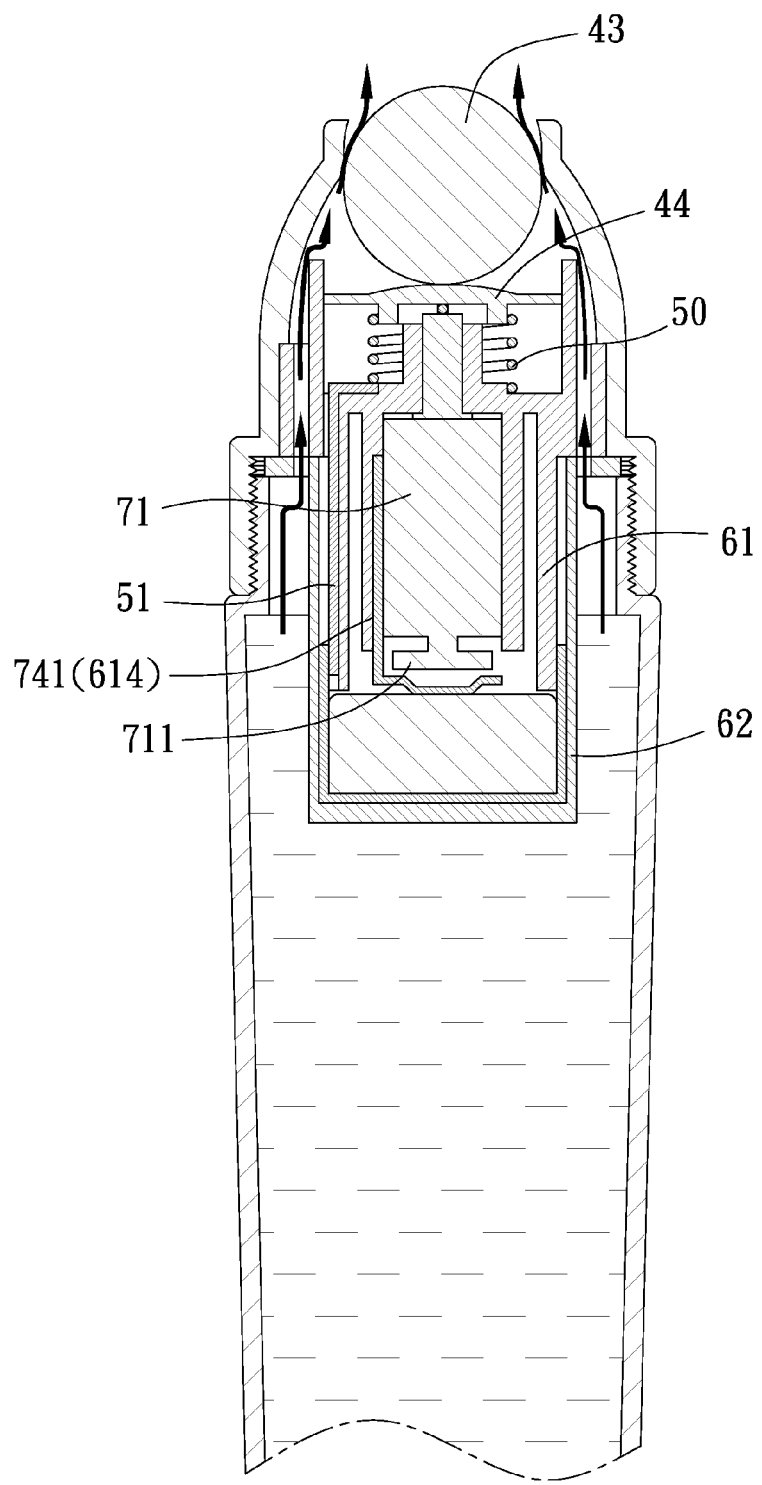
FIG. 7 is an assembled cross-sectional view showing a first conductive portion according to the second embodiment of the present invention.

The elastic body 50 is a compression spring and is disposed between the ball 43 and the accommodating unit 60. In addition to providing an elastic force upon the ball 43, two opposite ends of the elastic body 50 are provided with a first conductive portion 51 and a second conductive portion 52 respectively. The first conductive portion 51 is brought into electrical contact with a positive electrode (or negative electrode) of a power source of the electronic unit 70. The first conductive portion 51 may be integrally formed on the distal end of the elastic body 50 as shown in FIG. 7, or be separated from the elastic body 50 as shown in FIGS. 3 to 5. When the elastic body 50 is not pressed, the second conductive portion 52 is located above the negative electrode (or positive electrode) of a power source of the electronic unit 70 by a suitable distance. Further, a supporting base 44 is provided between the ball 43 and the elastic body 50. The outer surface of the supporting base 44 allows the ball 43 rest thereon. The internal space of the supporting base 44 allows the second conductive portion 52 of the elastic body 50 to be positioned therein.

The accommodating unit 60 comprises an accommodating body 61 and an accommodating base 62. The accommodating body 61 is formed into a rod. The outer periphery of the accommodating body 61 is provided with a first accommodating portion 611 for allowing the first conductive portion 51 to be disposed therein. Above an inner axial center of the accommodating body 61, a second accommodating portion 612, a third accommodating portion 613 and a fourth accommodating space 614 are provided in communication with each other for allowing the components of the electronic unit 70 to be assembled therewith. The accommodating base 62 is a hollow sleeve. The accommodating body 61 is disposed in the accommodating base 62, and then the accommodating base 62 is disposed across the inner periphery of the mouth of the bottled body 41.

The electronic unit 70 is configured to generate vibration, light or heat by means of the electrical conduction of its circuit. Two examples of the electronic unit 70 are described as follows.

In a first example, the electronic unit 70 includes a motor 71, a battery 72 serving as a power source, a first conductor 73, a second conductor 74, and a third conductor 75. The first conductor 73 is disposed in the second accommodating portion 612. One end of the first conductor 73 protrudes from the second accommodating portion 612 to face the second conductive portion 52. The motor 71 is assembled in the third accommodating portion 613, and the outer periphery of the motor 71 is electrically conductive. One end of the motor 71 corresponding to the first conductor 73 is formed into a plane for electrically contacting the first conductor 73. The other end of the motor 71 is provided with a vibrating shaft 711. The second conductor 74 is substantially formed into an L shape. One end of the second conductor 74 is brought into electrical contact with the surface of a negative electrode (or positive electrode) of the battery 72. The other end of the second conductor 74 is provided with an electrical connection portion 741 protruding upwards to be located in the fourth accommodating portion 614 and brought into electrical contact with the outer surface of the motor 71. With this structure, an electrical current flows from the negative electrode of the battery 72 through the motor 71 to the first conductor 73. The third conductor 75 is formed as a cap for allowing the battery 72 to be received therein, thereby electrically contacting the positive electrode (or negative electrode) of the battery 72 with the third conductor 75. The first conductive portion 51 of the elastic body 50 penetrates the first accommodating portion 611 to be brought into electrical contact with the third conductor 75.

When the user intends to use the liquid in the bottle container, the ball 43 is brought into contact with the skin of the user, thereby compressing the elastic body 50. As a result, the second conductive portion 52 is brought into contact with the first conductor 73 of the positive electrode (or negative electrode) of the power source, thereby achieving an automatic electrical conduction of the power circuit. In this way, the bottle container can turn on the motor 71 automatically to generate vibration.

Figure 6:
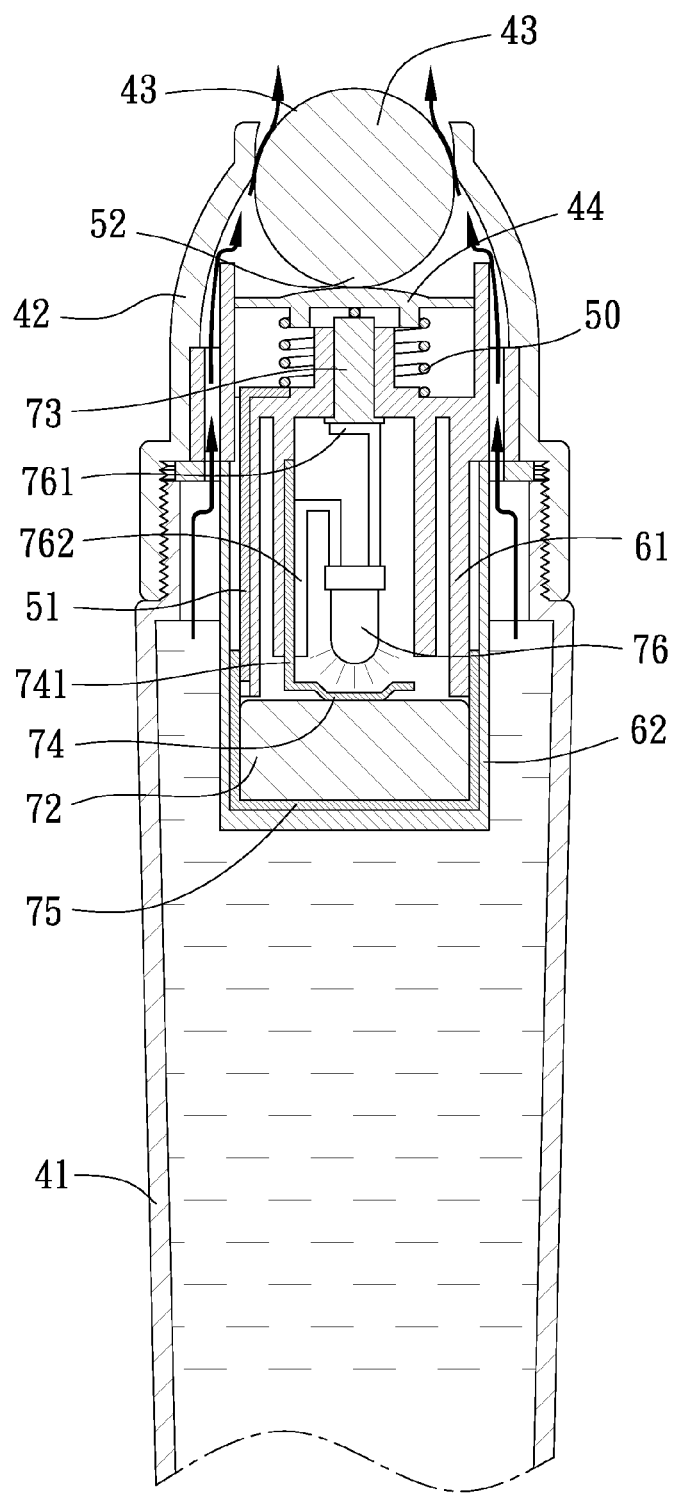
FIG. 6 is an assembled cross-sectional view of a second embodiment of the present invention in which the power source is electrically connected.

Please refer to FIG. 6. In the second example, the electronic unit 70 includes a lamp 76, a battery 72 serving as a power source, a first conductor 73, a second conductor 74, and a third conductor 75. The first conductor 73 is disposed in the second accommodating portion 612. One end of the first conductor 73 protrudes from the second accommodating portion 612 to face the second conductive portion 52. The lamp 76 is assembled in the third accommodating portion 613. The lamp 76 has a first leg 761 and a second leg 762. The first leg 761 is electrically connected to the first conductor 73, and the second leg 762 is electrically connected to the second conductor 74.

The third conductor 75 is also formed as a cap for allowing the battery 72 to be received therein in such a manner that the positive electrode (or negative electrode) of the battery 72 is brought into electrical contact with the third conductor 75. The second conductor 74 is substantially formed into an L shape. One end of the second conductor 74 is brought into electrical contact with the surface of the negative electrode (or positive electrode) of the battery. The other end of the second conductor 74 protrudes to form an electrical conduction portion 741 to electrically connect to the second leg 762. With this structure, an electrical current flows from the negative electrode of the battery 72 through the lamp 76 to the first conductor 73. The first conductive portion 51 of the elastic body 50 penetrates the first accommodating portion 611 to be brought into electrical contact with the third conductor 75 of the positive electrode (or negative electrode) of the power source.

When the user intends to use the liquid in the bottle container, the ball 43 is brought into contact with the skin of the user, thereby compressing the elastic body 50. As a result, the second conductive portion 52 is brought into contact with the first conductor 73 of the positive electrode (or negative electrode) of the power source, thereby achieving an electrical conduction of the power circuit automatically. In this way, the bottle container can turn on the lamp 76 automatically to generate light, thereby re-arranging the molecules of the liquid.

With the above-mentioned structure, the embodiment of the present invention utilizes the first conductive portion 51 and the second conductive portion 52 of the elastic body 50 as well as the electrical conduction of the first conductor 73, the second conductor 74 and the third conductor 75. Thus, the embodiment of the present invention can generate an electrical conduction of the power circuit automatically without a manual switch. The present invention has a compact construction and is more practicable and convenient. The vibration of the motor, the light of the lamp or the heat generated by the electronic unit 70 can increase the convenience and usability of the present invention.

Although the present invention has been described with reference to the foregoing preferred embodiments, it will be understood that the invention is not limited to the details thereof. Various equivalent variations and modifications can still occur to those skilled in this art in view of the teachings of the present invention. Thus, all such variations and equivalent modifications are also embraced within the scope of the invention as defined in the appended claims.

What is claimed is:

1. An automatic switch for a power circuit of a bottle container, the bottle container including a bottle body, a cover and an electronic unit, the cover enabling an accommodating unit to be assembled between the bottle body and the cover,
wherein a liquid is received in the bottled body, a ball is disposed in a mouth at a front end of the cover, the ball capable of opening and closing the mouth by means of an elastic body, the elastic body having a first conductive portion and a second conductive portion, the first conductive portion brought into electrical contact with a first electrode of a power source of the electronic unit, the second conductive portion located above a second electrode of the power source of the electronic unit by a distance when the elastic body is not pressed, and pressing the ball causes the second conductive portion to electrically contact the second electrode of the power source of the electronic unit.

2. The automatic switch for a power circuit of a bottle container according to claim 1, wherein a supporting base is provided between the ball and the elastic body, the ball abutting against an outer surface of the supporting base, and the second conductive portion of the elastic body is located in an internal space of the supporting base.

3. The automatic switch for a power circuit of a bottle container according to claim 1, wherein the accommodating unit includes an accommodating body and an accommodating base, the accommodating body provided with a plurality of accommodating portions for allowing the first conductive portion of the elastic portion and components of the electronic unit to be received therein, and the accommodating portions and the accommodating body are disposed inside the accommodating base.

4. The automatic switch for a power circuit of a bottle container according to claim 3, wherein the first conductive portion of the elastic body is integrally formed on a distal end of the elastic body or separated from the elastic body in such a manner that the first conductive portion is brought into electrical contact with the distal end of the elastic body.

5. The automatic switch for a power circuit of a bottle container according to claim 3, wherein the electronic unit includes a motor, a battery serving as a power source, a first conductor, a second conductor, and a third conductor, the accommodating body formed into a rod, an outer periphery of the accommodating body provided with a first accommodating portion for allowing the first conductive portion to be disposed therethrough; a second accommodating portion, a third accommodating portion and a fourth accommodating portion are formed above an inner axial center of the accommodating body for allowing the first conductor, the motor and an electrical conduction portion of the second conductor to be received therein, the first conductor disposed in the second accommodating portion, an end of the first conductor protruding from the second accommodating portion to face the second conductive portion, the outer periphery of the motor being electrically conductive, wherein one end of the motor corresponding to the first conductor is formed into a plane, another end of the motor is provided with a vibrating shaft, and the third conductor allows the battery to be received therein in such a manner that a first electrode of the battery is brought into contact with the third conductor, the second conductor substantially formed into an L shape, one end of the second conductor being brought into electrical contact with the surface of the second electrode of the battery, the other end of the second conductor being provided with an electrical connection portion for contacting the outer surface of the motor, an electric current flowing from the second electrode of the battery through the motor to the first conductor, and an outer surface of the third conductor is brought into electrical contact with the first conductive portion disposed through the first accommodating portion;
whereby, in using the liquid in the bottle container, the ball is brought into contact with skin of a user while the elastic body is pressed to cause the second conductive portion to be brought into electrical contact with the first conductor, thereby achieving an electrical connection of the power circuit and causing the bottle container to turn on the motor automatically to generate vibrations.

6. The automatic switch for a power circuit of a bottle container according to claim 3, wherein the electronic unit includes a lamp, a battery serving as a power source, a first conductor, a second conductor, and a third conductor, the accommodating body formed into a rod, an outer periphery of the accommodating body provided with a first accommodating portion for allowing the first conductive portion to be disposed therethrough; a second accommodating portion, a third accommodating portion and a fourth accommodating portion formed above an inner axial center of the accommodating body for allowing the first conductor and the lamp to be received therein, the first conductor disposed in the second accommodating portion, one end of the first conductor protruding from the second accommodating portion to face the second conductive portion, and the lamp has a first leg and a second leg, the first leg electrically connected to the first conductor, the second leg electrically connected to the second conductor, the third conductor allowing the battery to be received therein in such a manner that the first electrode of the battery is brought into electrical contact with the third conductor, wherein the second conductor is substantially formed into an L shape, one end of the second conductor brought into electrical contact with the surface of the second electrode of the battery, the other end of the second conductor protruding to form an electrical conduction portion to electrically connect to the second leg, an electrical current flowing from the second electrode of the battery through the lamp to the first conductor, and an outer surface of the third conductor is brought into electrical contact with the first conductive portion disposed through the first accommodating portion,
whereby, in using the liquid in the bottle container, the ball is brought into contact with skin of a user while the elastic body is pressed to cause the second conductive portion to be brought into electrical contact with the first conductor, thereby achieving an electrical conduction of the power circuit automatically and causing the bottle container to turn on the lamp to generate light, thereby re-arranging the molecules of the liquid.

* * * * *